United States Patent [19]

Kerber, Jr.

[11] 4,365,143

[45] Dec. 21, 1982

[54] ASSEMBLY FOR PREPARING AND DISPENSING INFANTILE DIETARY FORMULATION

[76] Inventor: William X. Kerber, Jr., Rte. 3, Box 50-A, Tuttle, Okla. 73089

[21] Appl. No.: 219,031

[22] Filed: Dec. 22, 1980

[51] Int. Cl.³ .............................................. F27D 11/00
[52] U.S. Cl. .................................. 219/401; 219/319; 219/437; 219/439; 219/440; 422/303
[58] Field of Search ............... 219/284, 288, 316, 319, 219/401, 431, 432, 433, 437, 436, 438, 439, 440; 422/300, 301, 302, 303; 99/331, 467

[56] References Cited

U.S. PATENT DOCUMENTS

| | | | |
|---|---|---|---|
| 1,114,023 | 10/1914 | Olney | 422/302 X |
| 1,344,326 | 6/1920 | Williams | 219/401 X |
| 2,141,516 | 12/1938 | Clements | 422/303 |
| 2,146,511 | 2/1939 | Pierce | 219/288 |
| 2,715,898 | 8/1955 | Michaelis et al. | 219/401 X |
| 2,837,625 | 6/1958 | Conlin et al. | 219/436 |
| 3,119,925 | 1/1964 | Shomock | 219/288 |
| 3,347,618 | 10/1967 | McKeown | 422/302 |
| 3,814,901 | 6/1974 | Morhack | 219/401 |
| 4,084,080 | 4/1978 | McMahan | 219/401 |
| 4,123,969 | 11/1978 | Abbate | 99/467 |

FOREIGN PATENT DOCUMENTS 558486  6/1958  Canada .............................. 219/401

*Primary Examiner*—Volodymyr Y. Mayewsky
*Attorney, Agent, or Firm*—Laney, Dougherty, Hessin & Beavers

[57] ABSTRACT

An assembly for preparing and bottling liquid infant's formula, which assembly includes a steam basin having a water reservoir, and a heating element in the reservoir for boiling the water to yield steam, a graduated measuring pitcher invertible over and adapted for support upon the steam basin; and sterilization racks removably supported on the steam basin and dimensioned for containment within the measuring pitcher.

15 Claims, 7 Drawing Figures

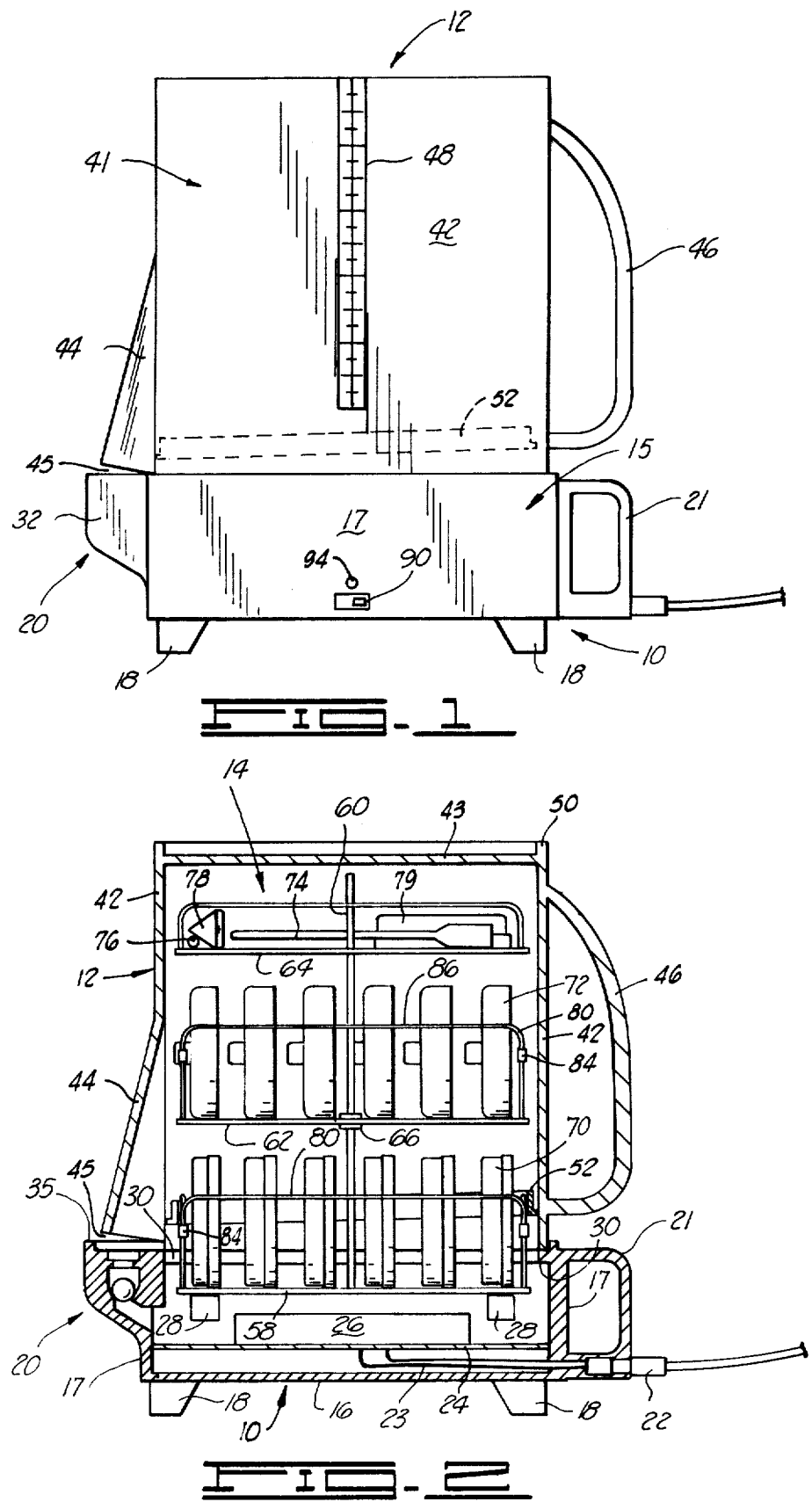

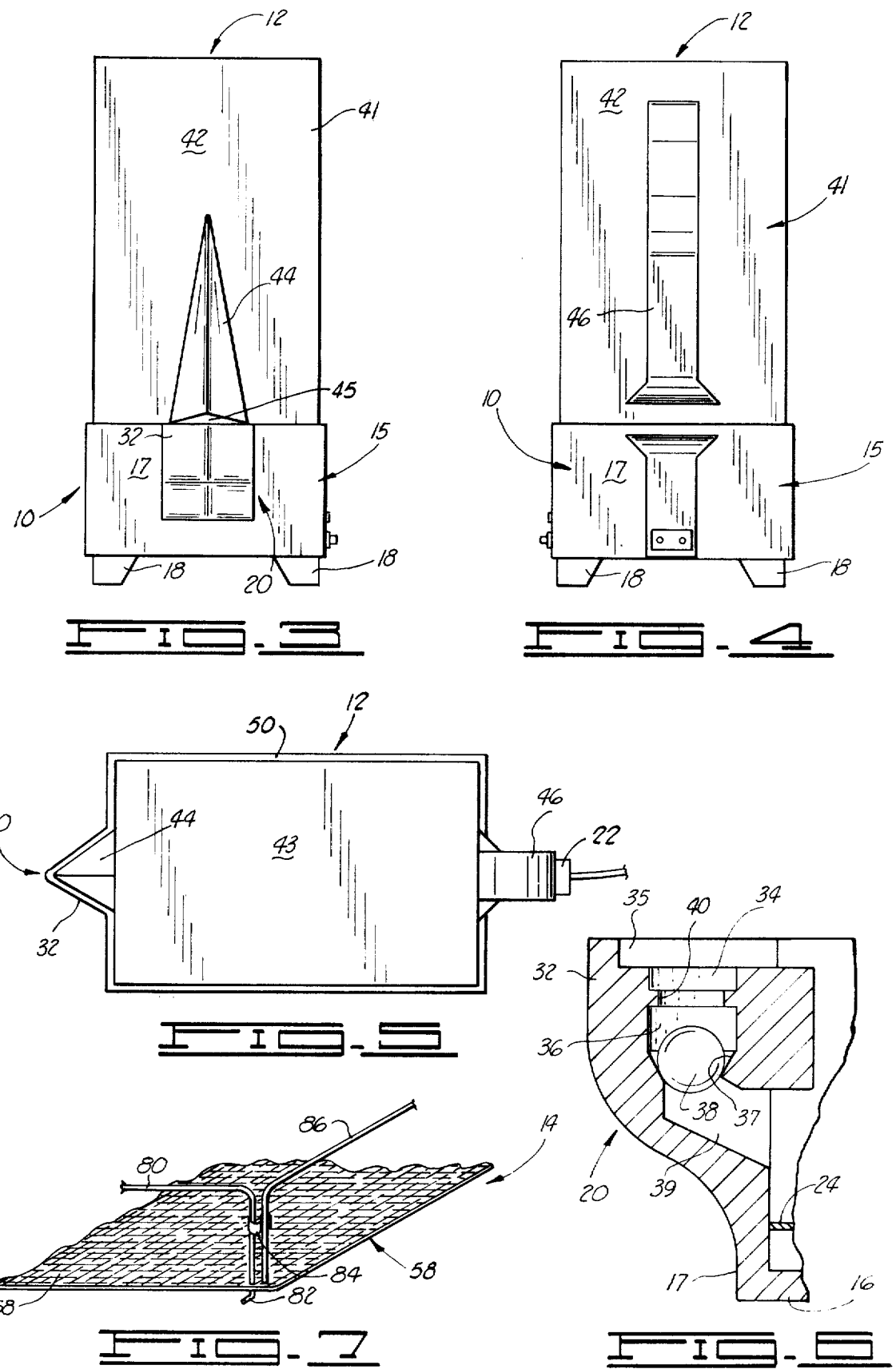

ASSEMBLY FOR PREPARING AND DISPENSING INFANTILE DIETARY FORMULATION

BACKGROUND OF THE INVENTION

This invention relates to an assembly for preparing and feeding the liquid formula fed to infants.

BRIEF DESCRIPTION OF THE PRIOR ART

A number of innovations have been forthcoming within recent years which are intended to aid new mothers in safely and quickly preparing formula to be used in the feeding of infants. Disposable bottles have come into widespread use and alleviate one concern of the past which entailed the tedious repeated sterilization and reuse of glass bottles used to contain the formula.

There have also been proposed various systems and assemblies which are intended to allow the nipples and caps employed upon the disposable bottles to be quickly sterilized, along with certain accessory implements such as tongs, stirrers and the like used in the sterilization process and in the preparation of formula. Such sterilization systems range from simple equipment in which the bottle caps and nipples are placed in an open pan of water in which they are then boiled for several minutes. They are then plucked out of the water and placed on bottles which have themselves by then been filled with formula made using other water boiled in another container. The pans employed frequently are whatever pans are available in the mother's kitchen equipment, and are not specifically designed or well adapted for sterilization or formula preparation. The open pans or pots containing boiling water evolving steam entail risks to the mother as she reaches for the nipples and caps with her tongs.

Some of the current sterilization systems are designed to accommodate the older reusable bottle formula containers, and therefore are both bulky and expensive by reason of the capacity required, and the precautions needed to assure that the glass is not broken in the course of sterilization.

In Conlin et al. U.S. Pat. No. 2,837,625, a sterilization system is described which includes a base member having a heating unit positioned therein for heating water contained in the base. The base is covered by means of a shell which forms a chamber. Within this chamber a major portion of the sterilizing operation takes place.

A similar patent is Shomock U.S. Pat. No. 3,119,925. In the Shomock system, a base member is provided which contains a heating element for heating water placed in the base. A cover encloses and defines a sterilizing area in which a rack is located for containing elements to be sterilized.

U.S. Pat. No. 2,146,511 to Pierce discloses a device which can be used for sterilizing bottles, and which includes a base which houses electrical heaters and a water well adapted to contain water which is boiled by means of the heaters. The base has a rim around the outer periphery thereof to receive the lower edge of a cover which is placed over the base to trap and hold the steam while it is sterilizing bottles rested upon the base.

In U.S. Pat. No. 3,347,618 to McKeown, a sterilization system is provided which includes a base adapted to hold water in a reservoir which surrounds and covers an electrical resistance heating system which uses water as a part of the conductive path of the electrical circuit, and thereby causes boiling of the water. A rack is adapted to be rested upon supporting sockets formed in the walls of the base, and is configured to hold the bottles for baby formula, as well as other paraphernalia used in the assembling of the bottles and preparation of the formula, if desired. At one side of the base, a lip or spout is formed in one wall in order to vent steam from the system. A cover is shaped to place over the rack when the rack is rested in its sockets in the base, and the cover fits snugly within a rim or peripheral flange formed around the top of the base so as to more effectively contain sterilizing steam.

BRIEF DESCRIPTION OF THE PRESENT INVENTION

Broadly described, the apparatus of this invention comprises a steam basin subassembly in which steam used for sterilization purposes is produced by boiling water which is thereby made ready for use in blending formula for the infant. A graduated measuring pitcher is inverted over, and supported on, the steam basin subassembly, and is dimensioned to sealingly engage the steam basin subassembly to receive and contain steam evolved therefrom. A sterilizing rack subassembly is supported on the steam basin subassembly within the measuring pitcher, and includes racks or grids for supporting implements used in the process of sterilizing and assembling component elements of the baby's formula bottle. These implements are all contained within the confines of the inverted pitcher. The pitcher includes a pouring lip which registers with a steam trap-pouring spout carried on the steam basin subassembly whereby a part of the steam from the interior of the pitcher is safely returned to a point of condensation within the basin assembly. A small portion of the steam is vented to the atmosphere through a small space between the pouring lip and the steam trap-pouring spout.

The described system permits the preparation of infant's liquid nutrient formulations using a single apparatus to achieve both preparation and mixing of the liquid formula composition, and also sterilization of the nipples, caps and handling equipment used in preparing the formula.

An object of the invention is to provide a relatively inexpensive, lightweight and compact assembly which can be used for sterilizing tongs, nipples, caps, can openers, stirrers and all other paraphernalia and equipment used in the preparation of baby formula, and at the same time, and in the course of such sterilization, to make the hot, boiled water which is needed for compounding the final liquid formula composition which will be fed to the infant.

Another object of the present invention is to provide an assembly useful in the sterilization of the equipment used in feeding liquid formula to infants, and to enable such apparatus to be used quickly and easily without special training or skill, and in a way such that the user of the equipment undergoes little risk of being scalded or burned during the sterilization and formula preparation steps followed in using the apparatus.

In addition to the described objects and advantages of the invention, additional objects and advantages will become apparent as the following detailed description of a preferred embodiment of the invention is read in conjunction with the accompanying drawings which illustrate such preferred embodiment.

BRIEF DESCRIPTION OF THE DRAWINGS

FIG. 1 is a side elevation view of the assembly for preparing apparatus for dispensing baby formula constructed in accordance with the present invention.

FIG. 2 is a vertical sectional view through the center of the apparatus assembly shown in FIG. 1.

FIG. 3 is the assembly illustrated in FIG. 1, but pivoted through 90° so that one other side of the assembly from that shown in FIG. 1 is shown in elevation.

FIG. 4 is a side elevation view similar to that of FIG. 3, but illustrating the assembly of the invention as it appears on the opposite side thereof from that which is shown in FIG. 3.

FIG. 5 is a plan view of the apparatus illustrated in FIG. 3.

FIG. 6 is an enlarged detail view, in section, showing a steam trap-pouring spout structure forming a part of a steam basin subassembly used in the invention.

FIG. 7 is a detail view, in perspective, of a corner portion of a part of the sterilizing rack subassembly utilized in the invention.

BRIEF DESCRIPTION OF A PREFERRED EMBODIMENT OF THE INVENTION

Referring initially to FIG. 1 of the drawings, the assembly for sterilizing and preparing apparatus for feeding formula to infants includes a steam basin subassembly, designated generally by reference numeral 10, and a graduated measuring pitcher subassembly, designated generally by reference numeral 12 and shown inverted over, and supported upon, the steam basin subassembly. Positioned within the measuring pitcher subassembly 12 and also supported on bracket structures within the steam basin subassembly 10 is a sterilizing rack subassembly, designated generally by reference numeral 14.

The steam basin subassembly 10 includes a generally rectangular housing 15 which has a horizontally extending bottom wall 16 and a plurality of vertically extending side walls 17. The housing 15 is supported on a plurality of legs 18 adapted to rest upon any suitable structure, such as a table or the like. Extending outwardly from one side of the housing 15 is a steam trap-pouring spout structure, designated generally by reference numeral 20. At its opposite side, the housing 15 has a handle 21 secured thereto and projecting outwardly from a side wall 17. The bottom portion of the handle 20 which extends horizontally encloses electrical conductors 23. The conductors terminate in a recessed plug on the outer side of the handle 21 for receiving an electrical socket 22 providing electrical power to the steam basin subassembly 10. The electrical conductors 23 also extend through the space provided between the bottom 16 and a heater supporting basin floor 24 which supports on its upper side an electrical resistance heater 26 supplied with power by the conductors.

A plurality of support brackets 28 are secured to the inner surfaces of the side walls 17 of the housing 15 and function to support the sterilization rack subassembly 14 within the steam basin subassembly housing 15 in a manner and for a purpose hereinafter described. The side walls 17 of the housing 15 terminate in upper edges. Spaced downwardly from the several upper edges of the side walls 17 is an upwardly projecting flange 30 located on each of the side walls so as to provide a supporting ledge extending entirely around the housing.

The configuration and construction of the steam trap-pouring spout structure 20 is best illustrated in FIGS. 3, 5 and 6. Reference to these figures shows that the steam trap-pouring spout structure includes a housing 32 which is generally V-shaped in horizontal configuration and defines, at its upper end, an opening 34 (see FIG. 6). The opening 34 is surrounded by a peripheral flange 35 which has an upper edge in coplanar alignment with the upper edges of the side walls 17 of the housing 15 of the steam basin subassembly 10 as illustrated in FIGS. 2 and 6. The opening 34 communicates with a bore 36 through the housing 32 and with an opening through a valve seat 37. A spherical valve element 38 is gravity seated on the seat 37 when the assembly of the invention is in the status depicted in FIGS. 1–5. On the opposite side of the valve seat 37 from the bore 36, a passageway 39 communicates with the hollow interior of the housing 15 at a location above the basin floor 24.

For the purpose of preventing loss of the spherical valve element 38 when liquid is poured from the steam basin out through the steam trap-pouring spout structure 20, a spider 40 is provided in extension across the bore 36 to arrest outward movement of the valve element.

The graduated measuring pitcher subassembly 12 forming a portion of the invention includes a pitcher or open-topped container designated generally by reference numeral 41 and having a plurality of sides 42 making the pitcher substantially rectangular in configuration. The pitcher also includes a bottom 43 opposite the open top which is defined by the free edges of the sides 42. An opening is formed in one of the sides 42 of the pitcher 41 in alignment with a generally pyramidally shaped pouring lip 44. The pouring lip 44 is defined by a pair of divergent sides as best illustrated in FIG. 3, and has an opening between these sides which is generally aligned with the open top of the pitcher 41, but which lies in a plane sloping downwardly from the plane of the container opening so that the edges of the sides 42 slant upwardly from the housing 32 to form a steam vent aperture 45. The pouring lip 44 is configured so that steam may be directed through the pouring lip towards the opening 34 formed in the housing 32 of the steam trap-pouring spout structure 20 carried on the steam basin subassembly 10 at a time when the graduated measuring pitcher subassembly 12 is inverted over the steam basin subassembly. This relationship is illustrated in FIGS. 1–5. It will be noted that the free upper edges of the sides 42 of the pitcher 41 terminate in coplanar alignment so that the pitcher may be sealingly supported in an inverted position upon the inwardly projecting flange 30 carried on the inner sides of the vertically extending side walls 17.

At its side opposite that side thereof to which the pouring lip 44 is attached, the pitcher 41 has a handle 46 secured thereto. In a preferred embodiment of the invention, the pitcher 41 is formed of a transparent plastic material which will permit the liquid contents of the pitcher to be viewed through the walls thereof. To the end of permitting the amount of liquid in the container to be known when this construction is employed, a graduated scale 48 is provided which extends upwardly along one side 42 of the pitcher 41. In similar fashion, a scale may also be provided, if needed, on the inner surface of one of the sides 42 of the pitcher 41 (as in the case where the pitcher is not transparent) to permit the liquid level to be gauged.

A supporting rim 50 is extended peripherally around the bottom 43 of the pitcher 41 by extension of the sides 42 past the bottom, thus providing a supporting element for the pitcher when it is inverted. A condensate channel 52 is secured to the inner surface of the sides 42 and extends around the pitcher to a point of termination adjacent the pouring lip 44.

The sterilization rack subassembly 14, which is positioned within the graduated measuring pitcher subassembly 12 when the assembly is in the operative position illustrated in FIGS. 1–5 of the drawings, is illustrated in detail in FIGS. 2 and 7. The sterilization rack subassembly 14 includes a reticulated steam-permeable base grid 58 which is rectangular in configuration and dimensioned to fit down within the housing 15 of the steam basin subassembly 10. The base grid 58 rests upon the support brackets 28. Projecting upwardly from the center of the base grid 58 is a vertical support rod 60 which supports an intermediate reticulated steam-permeable grid 62 spaced vertically from the base grid 58, and a reticulated, steam-permeable top grid 64 which is spaced vertically from the intermediate grid 62. The intermediate grid 62 is mounted on the vertical rod 60 by a suitable journal or bearing structure 66 to permit it to be rotated about the axis of the rod 60 for a purpose hereinafter described. Each of the grids 58, 62 and 64 is, as indicated, steam-permeable, and to that end, can be constructed of heavy wire mesh 68 having openings between the criss-crossed wire elements forming the grid as shown in FIG. 7. The wire elements may be coated with plastic if desired.

It will be noted in referring to FIG. 5 that the shape of the pitcher 41, as viewed in bottom plan view, is rectangular, and that the pitcher is substantially greater in dimension between two of its parallel sides than it is between the other two sides. This same configuration is characteristic of each of the steam-permeable reticulated grids or racks 58, 62 and 64. Thus, their shape accommodates them to fit within the pitcher 41 of the graduated measuring pitcher subassembly 12. This configuration also enables another important result to be achieved, however, which is rotation of the intermediate reticulated grid 62 upon the bearing structure 66 by which it is supported on the vertical support rod 60 so that the ends of the rectangular base grid 58 are exposed, and the opposite ends of the intermediate grid 62 are also exposed as this grid is rotated 90°, and, by reason of its rectangular shape, comes to form a cross-shaped configuration when viewed in plan in conjunction with the base grid 58 and top grid 64.

By rotating the intermediate grid 62 prior to the time that the sterilizing rack subassembly 14 is placed in its housed position in the relationship to the other subassemblies shown in FIG. 2, the intermediate grid 62 is turned out so as to expose its opposite end portions in the manner described, and the several reticulated, steam-permeable grids are then loaded with various parts of the cap subassembly secured to a disposable formula bottle used for feeding infants. Thus, as an illustrated example of such loading, and following reorientation of the intermediate grid 62 into alignment with the base grid 58 and the top grid 64, the base grid carries protective overcaps 70 of the type which are snapped over the top of disposable bottles. The intermediate grid 62 is loaded with rubber nipples 72 which are aligned and rest upon the wire mesh 68 of the intermediate grid. As will be understood, such nipples are clamped in sealed relation to the top of the disposable bottle by means of a threaded retainer ring after formula has been poured into the bottles as they are made ready for feeding the infant. Upon the wire mesh grid of the top grid 64, tongs 74 and other implements, such as a stirrer 76 and can opener 78, used in handling the nipples 72 and caps 70, are rested, and are immediately accessible to the preparer of the baby's formula at such time as the pitcher 41 is lifted up, following sterilization, to expose the sterilizing rack subassembly 14. One of the described threaded retainer rings 79 previously described is also shown resting upon the top grid 64.

It will be noted in referring to FIG. 7 that the construction of each of the reticulated, steam-permeable grids 58 and 62 further includes a detachable, U-shaped side gate rod 80 which is pivotally engaged with the wire mesh 68 by a pair of toes 82. A spring clip bracket 84 enables the gate rod 80 to be held in an upright retaining position when the clip bracket 84 is snap-engaged with an end retaining rod 86 which extends along one of the shorter sides of each of the grids 58 and 62, and substantially normal to the gate rod 80. When the gate rod 80 is swung down to a lowered position during loading of each of the grids 58 and 62, easier access can be had to the interior portions of each grid, thus facilitating placement of the caps 70 and nipples 72 in the manner illustrated in FIG. 2.

USE AND OPERATION OF THE INVENTION

In the utilization of the assembly for preparing and bottling liquid infant's formula, the user of the apparatus will initially remove and invert the pitcher 41 to an upright position. The sterilizer rack subassembly 14 will also be carefully lifted and removed from its position of rest upon the steam basin subassembly 10 by grasping the upper end of the vertical support rod 60 and lifting it upwardly. There will not, of course, be any of the nipples 72 or caps 70 on the several grids 58 and 62 at this time.

After the pitcher 41 has been removed and inverted, and the sterilizer rack subassembly 14 has also been removed, water is placed in the housing 15 of the steam basin. In general, the amount of water used will be enough to provide the water content required in the mixing of the baby's formula, plus some additional hot water for sterilization of the formula can and of the steam trap-pouring spout structure at a time, and for the reasons, hereinafter described. The amount of water added to the rectangular housing 15 of the steam basin subassembly 10 will also generally be an amount sufficient to cover the heater 26.

Either before or after placing the described amount of water in the steam basin subassembly 10, the nipples 72, over caps 70, retainer rings 79, and the accessory implements employed in assembling the formula bottle and stirring the formula will all have been washed in hot soapy water and rinsed. After this, the nipples 72 are placed on the intermediate grid as hereinbefore described while this grid has been rotated 90° from its illustrated position in FIG. 2 to provide access to opposite ends thereof. The over caps 70 will be placed on the base grid 58 as also shown in FIG. 2. After this placement by the use of the tongs 74, the tongs, can opener 78, stirrer 76 an retainer ring 79 are all placed upon the top grid 64. The sterilizing rack subassembly 14 is then returned to its position illustrated in FIG. 2 in which it rests upon the support brackets 28.

After the sterilizing rack subassembly 14 is thus placed in position over the steam basin subassembly 10 ontaining water in the housing 15, the graduated measuring pitcher subassembly 12 is inverted and is placed over the sterilizing rack subassembly so as to enclose it and to form a seal around it at the location where the edges of the sides 42 thereof meet and rest upon the inwardly projecting flanges 30. It will be noted that in positioning the pitcher 41 upon the flanges 30, the pitcher is oriented so that the pouring lip 44 is aligned with the steam trap-pouring spout structure 20 carried on the steam basin subassembly 10. In this position, the pouring lip 44 of the pitcher is located directly over the opening 34 formed through the upper side of the housing 32 of the steam trap-pouring spout structure.

After performing the foregoing described manipulations, and assembling the various parts of the invention in the position relative to each other illustrated in FIG. 1 of the drawings, the electrical plug 22 is inserted into the socket provided in the handle 21, and a plug (not shown) at the other end of a power cord is connected to a wall socket in conventional fashion. Power is thus supplied to the steam basin subassembly 10. The switch 90 is then pressed to start current flowing to the electrical resistance heater 26 via a thermostat (not shown) which, for example, is utilized in conjunction with a suitable relay system to open the circuit to the heater after the water above the basin floor 24 has been brought to a temperature of 100° C., and maintained at that temperature for a time period of five minutes. Normally, heating the water to this temperature for this time period will provide adequate steam to accomplish the sterilization of the implements and parts of the disposable bottle assembly carried upon the sterilizer rack subassembly 14.

After the start switch 90 has been pressed, the heater 26 commences to heat the water carried in the housing 15 of the steam basin subassembly 10. When the water has been brought to a boil, steam rises from the water in the steam basin subassembly and ascends upwardly into the interior of the pitcher 41 forming a portion of the graduated measuring pitcher subassembly 12. At this location, the steam comes in contact with the over caps 70 and the rubber nipples 72, as well as with the handling tongs 74, can opener 78 and stirring rod 76 carried on the top grid 64. In a short time, the steam, by contact with these devices contained on the sterilizing rack subassembly within the pitcher 41, has sterilized all of these implements and parts.

In order to partially vent the steam being produced in this fashion, and yet prevent all of the steam being released to the atmosphere and possibly constituting a source of injury to one contacting it at that time, the steam passes through the pouring lip 44 to the steam vent aperture 45. A part of the steam condenses, however, and the condensate gravitates through the opening 34 in the housing 32 of the steam trap-pouring spout structure 20, and accumulates in the space 36 over the spherical valve element 38. Steam which condenses on the inner sides of the walls 42 of the pitcher 41 is also channeled ultimately to this location by the condensate channel 52 and the pouring lip 44. A substantial amount of the condensed steam can be accommodated in the bore 36.

After sterilization of the elements contained on the sterilizing rack subassembly 14 has been completed, the thermostatic control will shut off the power to the heater 26. The unit will then continue to cool until the temperature of the water in the housing 15 reaches a level slightly higher than that which is to characterize the final formulation. This will be indicated by the light 94 associated with the thermostatic control turning off. The unit is now indicated to be safe, and the heated water in the housing 15 ready for use in mixing the formula. The electric socket 22 is then disconnected.

The pitcher 41 is next removed by grasping the handle 46 and inverting the pitcher, being careful not to upset the sterilizing rack subassembly 14 in so doing. When the pitcher 41 has been removed and inverted, the sterilizing rack subassembly 14 is then carefully removed by lifting upwardly by gripping the top end of the vertical support rod 60 in the manner hereinbefore described. The sterilizing rack subassembly 14 is then set gently down on a countertop or the like.

The can of formula concentrate which is to be mixed with water to prepare the final formula used in feeding the infant is next set close at hand. The steam basin subassembly 10 is then lifted upwardly by the handle 21, and is tilted so that the hot water contained therein runs toward the side of the housing 15 upon which the steam trap-pouring spout structure 20 is located. It will be noted in referring to FIG. 6 of the drawings that the construction of the steam trap-pouring spout structure 20 is such that, as the housing 15 is tilted by manipulating the handle 21, the spherical valve element 38 becomes unseated, and the hot water can pass through the opening in the valve seat 37 into the bore 36 and out past the peripheral flange 35. Of course, ahead of this hot water which has previously been isolated from the steam trap-pouring spout structure 20, the condensate produced by condensation of the steam above the valve element is poured out and is the first water to be discharged through the opening 34.

Immediately after starting to pour the boiling water out of the housing 15 via the steam trap-pouring spout structure 20, the water is directed over the top of the can which contains the formula concentrate to sterilize the can at this location. The can opener 78 is next removed from the top grid 64 of the sterilizing rack subassembly 14 and used to pierce the can containing the formula concentrate to permit it to be dispensed.

The formula concentrate from the can is next poured into the pitcher 41 of the graduated measuring pitcher subassembly 12. The interior of this pitcher has, of course, previously been thoroughly sterilized by contact of steam with the interior of the pitcher. After the formula concentrate has been poured into the pitcher 41, hot water from the housing 15 of the steam base subassembly 10 is poured out of the steam trap-pouring spout structure 20 into the pitcher 41 until the total liquid level in the pitcher rises to the appropriate graduation on the pitcher. After this has been accomplished, the stirrer 76 is removed from the top grid 64 and used to thoroughly stir and mix the formula concentrate with the hot sterile water poured into the pitcher 41 from the steam basin subassembly 10. Finally, the tongs 74 are used to transfer the nipples 72 to a disposable formula bottle from the intermediate grid 62 after this grid has been swung sideways through 90° in the manner hereinbefore described. The tongs are then used to place the over caps 70 and retainer ring 79 on the bottles.

From the foregoing description of the invention, it will be apparent that the assembly of the invention is a system which enables the economic, rapid and safe sterilization and concurrent preparation of those elements needed to yield, as the final product, contained formula ready for feeding to an infant from a sterile and safe system. The use of the apparatus is relatively easy, and little opportunity exists for a mother employing the apparatus to become burned by steam, or by the heating element which is used.

Although various changes can be effected in the specific structures employed in the assembly of the invention, and in the way in which these structures are arranged relative to each other, any changes of form and arrangement which are made without relinquishment of the basic principles upon which the invention is based, and which are herein set forth in detail, are deemed to be circumscribed by the spirit and scope of the invention except as the same may be necessarily limited by the appended claims or reasonable equivalents thereof.

What is claimed is:

1. An apparatus for preparing and for dispensing infant formula comprising:
   a steam basin subassembly including:
      a reservoir for formula water containment;
      heating means in said reservoir;
      handle means for pouring hot, uncontaminated formula water out of said reservoir into a container means; and
      pouring means for cooperating with said handle means in the pouring of heated formula water out of said reservoir into a container means;
   container means having an open top and inverted over, and supported on, said steam basin subassembly and suitable for mixing formula therein;
   sterilizing rack means removably positioned at least partially within said container means and over said steam basin subassembly;
   lip means on said container means for directing condensed steam from said container means downwardly toward said steam basin subassembly and for pouring liquid from said container means during formula preparation; and
   trap means on said water reservoir for receiving steam from said steam directing means and for condensing the received steam at a location isolated from the water in the water reservoir.

2. An apparatus as defined in claim 1 wherein said container means comprises:
   a graduated pitcher; and
   a handle at one side of said pitcher on the opposite side thereof from said steam directing means.

3. An apparatus as defined in claim 1 wherein said trap means is formed integrally with said pouring means.

4. An apparatus as defined in claim 1 wherein said pouring means comprises a steam trap-pouring spout subassembly including:
   a space for receiving condensed steam from said container means; and
   valve means for isolating said space from said reservoir.

5. An apparatus as defined in claim 1 wherein said container means comprises:
   a pitcher adapted for mixing nutrient formulation for infants therein and having:
      a handle on one side of the pitcher; and
      a pouring lip aligned with, and adjacent, said pouring means.

6. An apparatus as defined in claim 5 and further characterized as including a condensate channel around the inner side of said pitcher and positioned to convey condensed steam from the walls of the pitcher to said pouring lip.

7. An apparatus as defined in claim 6 wherein said pouring means comprises a steam trap-pouring spout subassembly including:
   a space for receiving condensed steam from said container means; and
   valve means for isolating said space from said reservoir.

8. An apparatus as defined in claim 6 wherein said sterilizing rack means comprises:
   a plurality of vertically spaced wire mesh grids of generally rectangular configuration and including at least one intermediate grid between the uppermost of said grids and the lowermost of said grids; and
   a vertically extending support rod supporting said grids in vertically spaced relation to each other and rotatably supporting said intermediate grid for rotation about the axis of said vertically extending support rod.

9. An apparatus as defined in claim 8 wherein said sterilizing rack means further comprises a gate rod pivotally connected to each of said wire mesh grids and pivotable from a vertically extending retaining position normal to said wire mesh grid to a downwardly pivoted position.

10. An apparatus for preparing and dispensing infant's formula from a sterile container comprising:
    a steam basin subassembly including:
       a housing having vertically extending side walls, and having a flange projecting inwardly from the side walls adjacent the upper edges thereof;
       a steam trap-pouring spout structure on one of the side walls of the housing and defining a hollow interior communicating with the interior of the housing, said steam trap-pouring spout structure including a check valve isolating a space for accommodating condensed steam from the interior of the housing;
       heating means in said housing;
       a handle on said housing for pouring hot water from the housing out through said steam trap-pouring spout structure;
    a graduated measuring pitcher subassembly over said steam basin subassembly and supported on said flange, said graduated measuring pitcher subassembly including:
       a pitcher having volumetric graduated scale means thereon; and
       means for directing condensed steam into said steam trap-pouring spout from the interior of the pitcher;
    a sterilizing rack subassembly supported on said steam basin subassembly independently of said graduated measuring pitcher assembly, and enclosed within said pitcher and;
    implements used in assembling said nipples to bottles carried detachably on said sterilizing rack subassembly.

11. An apparatus as defined in claim 10 wherein said sterilizing rack subassembly comprises:
    a plurality of steam-permeable supporting means; and
    means for pivotally supporting said steam-permeable supporting means for pivotation about a vertical axis and in vertically spaced relation to each other.

12. An apparatus as defined in claim 11 and further characterized as including means for automatically de-energizing said heating means after a predetermined time period.

13. An apparatus for sterilizing paraphernalia used in the preparation of infant formula comprising:
   a steam basin subassembly including:
      a reservoir for water containment; and
      heating means in said reservoir;
   lid means having an open top and inverted over, and supported on, said steam basin subassembly; and
   sterilizing rack means removably positioned at least partially within said lid means and over said steam basin subassembly, said rack means comprising:
      a plurality of vertically spaced grids of generally rectangular configuration and including at least one intermediate grid between the uppermost of said grids and the lowermost of said grids; and
      a vertically extending support rod supporting said grids in vertically spaced relation to each other and rotatably supporting said intermediate grid for rotation about the axis of said vertically extending support rod.

14. An apparatus as defined in claim 13 wherein said sterilizing rack means further comprises a gate rod pivotally connected to each of said wire mesh grids and pivotable from a vertically extending retaining position normal to said wire mesh grid to a downwardly pivoted position.

15. An apparatus as defined in claim 13 wherein said pouring means comprises a steam trap-pouring spout subassembly including:
   a space for receiving condensed steam from said container means; and
   valve means for isolating said space from said reservoir.

* * * * *